(12) United States Patent
Wakasugi et al.

(10) Patent No.: US 6,849,419 B1
(45) Date of Patent: Feb. 1, 2005

(54) MONOCLONAL ANTIBODY HYBRIDOMA IMMUNOASSAY METHOD AND DIAGNOSIS KIT

(75) Inventors: Masahiko Wakasugi, Tokyo (JP); Ritsuko Mochida, Tokyo (JP); Haruhisa Hirata, Tokyo (JP)

(73) Assignee: Wakamoto Pharmaceutical Co., Ltd., Tokyo (JP)

( * ) Notice: Subject to any disclaimer, the term of this patent is extended or adjusted under 35 U.S.C. 154(b) by 85 days.

(21) Appl. No.: 10/111,650

(22) PCT Filed: Oct. 27, 2000

(86) PCT No.: PCT/JP00/07554

§ 371 (c)(1),
(2), (4) Date: Jul. 23, 2002

(87) PCT Pub. No.: WO01/32908

PCT Pub. Date: May 10, 2001

(30) Foreign Application Priority Data

Oct. 29, 1999 (JP) .............................. 11-308475
Feb. 28, 2000 (JP) .................................. 2000-052377
Aug. 11, 2000 (JP) ...................................... 2000-244414

(51) Int. Cl.$^7$ .............................................. C12N 15/02
(52) U.S. Cl. ........................ 435/7.32; 435/27; 435/14; 435/29; 435/4; 435/28; 435/34; 530/388.1; 530/388.2
(58) Field of Search .......................... 435/7.32, 27, 28, 435/192, 29, 264, 34, 278, 14, 262.5, 283.1, 4, 190, 26, 810; 530/388.1, 388.2

(56) References Cited

U.S. PATENT DOCUMENTS

| | | | | |
|---|---|---|---|---|
| 4,132,527 A | * | 1/1979 | Maekawa et al. ............. 436/66 |
| 5,030,717 A | * | 7/1991 | Tramontano et al. ....... 435/131 |
| 5,171,529 A | * | 12/1992 | Schreiber ..................... 422/58 |
| 5,702,911 A | * | 12/1997 | Whalen ........................ 435/12 |
| 6,005,090 A | * | 12/1999 | Doidge et al. .............. 536/23.5 |
| 6,051,416 A | * | 4/2000 | Pace et al. ................ 435/252.1 |
| 6,468,545 B1 | * | 10/2002 | Doidge et al. ............ 424/234.1 |
| 6,630,582 B1 | * | 10/2003 | Doidge et al. .............. 536/23.6 |
| 2004/0023316 A1 | * | 2/2004 | Reiter et al. ................ 435/7.32 |

FOREIGN PATENT DOCUMENTS

| | | | |
|---|---|---|---|
| EP | 0745674 | * | 12/1996 |
| EP | 0745674 A2 | | 12/1996 |
| EP | 0806667 A1 | | 11/1997 |
| WO | 95/27506 | * | 10/1995 |
| WO | 95/33482 | * | 12/1995 |
| WO | 98/06853 | * | 2/1998 |
| WO | WO00/26671 A1 | | 5/2000 |
| WO | 0127612 | * | 4/2001 ........... G01N/33/48 |

OTHER PUBLICATIONS

Dewhirst, FE et al, International Journal of systematic bacteriology, Jul. 1994, vol. 44(3), pp. 553–560,(abstract only).*
Fanti, L et al, Digestion, 1999, vol. 60, pp. 456–460.*
Firouzi et al, Gastroenterology, vol. 112(4 suppl.), p. A15, 1997 H.pylori gastritis and positive fecal occult blood test (abstract only).*

(List continued on next page.)

Primary Examiner—Lynette R. F. Smith
Assistant Examiner—Ginny Allen Portner
(74) Attorney, Agent, or Firm—Sughrue Mion, PLLC

(57) ABSTRACT

The object of the present invention is to provide a diagnostic method by which *Helicobacter pylori* infection can be diagnosed at low cost without causing pain on subjects and without requiring particular equipment and which is free of cross reactivity and excellent in specificity without variation among lots as a result of the use of a single antibody facilitating the quality control and which shows good sensitivity even when a single monoclonal antibody is used.

The present invention provides a monoclonal antibody which recognizes *Helicobacter pylori* catalase as an antigen.

9 Claims, 2 Drawing Sheets

OTHER PUBLICATIONS

Grubewl, Peter et al, Journal of Clinical Microbiology, Jun. 1997, vol. 35(6), pp. 1300–1303, Vector potenial of Houseflies (*Musca domestica*) for *Helicobacter pylori*.*

Hazenberg, MP et al, European Journal of Clinical investigation (England) Feb. 1989, vol. 19(1), pp. 61–64, (abstract only).*

McLauchlin, J et al, Folia parasitologica (CZech Republic) 1998, vol. 45(2) pp. 83–95, (English abstract only).*

Namavar, F et al, European Journal of clinical microbiology and infectious diseases, 1995, vol. 14(3), pp. 234–237, (abstract only; cited relative enablement).*

Osaki, T etal, Journal of Clinical Microbiology, vol. 36(1), pp. 321–323, Jan. 1998, Detection of *Helicobacter pylori* in fecal samples of Gnotobiotic mice infected with *H.pylori* by an immunomagnetic–bead separation technique.*

Saunders, KE et al, Journal of Clinical Microbiology, vol. 37(1) Jan. 1999, pp. 146–151.*

On Stephen, LW et al, Systemic and Applied Microbiology, vol. 17(4), pp. 543–553, 1994, abstract only.*

Rolff, M et al, Ugeskrift for laeger (Denmark) Nov. 12, 1990, vol. 152(46) pp. 3468–3469 (English title only) Evaluation of the catalase reaction as a sign of pus in feces.*

Newell, DG et al, Basic and Clinical Aspects of *H.pylori* infection, 1994, pp. 223–226, The cloning and partial sequence analysis of the catalase gene of *Helicobacter pylori*.*

Buck, Fiona Jane, PH.D, 1998, Vaccine Therapy for chronic Helicobacter infection (cholera holotoxin) University of New South Wales (Australia), vol. 59(11–b) of Dissertation Abstrcts International, p. 5770 (abstract only).*

Newell, DG et al, Basic and Clinical Aspects of *H.pylori* infection, Springer Verlan Berlin Heidelberg, 1994, pp. 223–226, The cloning and partial sequence analysi of the catalase gene of *Helicobacter pylori*.*

Vaira, D et al, Alimentary pharmacology and therapeutics, Oct. 2000, vol. 14(suppl. 3), pp. 13–22), Review article, invasive and non–invasive tests for *Helicobactger pylori* infection.*

Journal of General Microbiology, vol. 137, No. 1, (1991), Staurt L. Hazell, et al., "*Helicobacter pylori* catalase", pp. 57–61.

Clinica Cheimica Acta, vol. 267, No. 2, (1997), Jun Cao, et al., "Detection of spiral and coccoid forms of *Helicobacter pylori* using a murine monoclonal antibody", pp. 183–196.

Journal of Bacteriology, Vo. 178, No. 23, (1996), Stefan Odenbreit, et al., "Cloning and Genetic Characterization of *Helicobacter pylori* Catalase and Construction of a Catalase–Deficient Mutant Strain", pp. 6960–6967.

* cited by examiner

MONOCLONAL ANTIBODY HYBRIDOMA IMMUNOASSAY METHOD AND DIAGNOSIS KIT

This is a National Stage Entry under 35 U.S.C. § 371 of PCT Application No. PCT/JP00/07554, filed Oct. 27, 2000.

TECHNICAL FIELD

The present invention relates to a monoclonal antibody recognizing *Helicobacter pylori* catalase as an antigen, a hybridoma producing said monoclonal antibody, an immunological assay method and a diagnosis kit.

BACKGROUND ART

*Helicobacter pylori* is a bacterial species found in the human gastric mucosa. The rate of *Helicobacter pylori* infection is closely related to social and economic factors, tending to be high in developing countries and low in advanced countries. However, the rate of infection among the Japanese is remarkably high among the advanced countries and it is even reported that 80% of people in and after the fourth decade of life have been infected. In recent years, it has been revealed that *Helicobacter pylori* may cause various gastric and duodenal diseases such as gastric ulcer, duodenal ulcer, chronic gastritis and, further, gastric cancer.

Since it was proven that the possibility of being afflicted by these diseases can be reduced by eradicating *Helicobacter pylori*, international discussions have been made about the diseases at which *Helicobacter pylori* eradication is to target. Thus, the diseases currently considered to be targets of such eradication include gastric ulcer, duodenal ulcer, malignant gastric lymphoma, residual stomach after resection due to early gastric cancer.

With the recognition of *Helicobacter pylori* eradication therapy as a novel method for the treatment of gastric and duodenal diseases, guidelines for therapeutic trials have been laid down and methods for diagnosis about occurrence of *Helicobacter pylori* infection and judgment about bacterial eradication have been proposed by the Japanese Society of Gastroenterology (The Japanese Journal of Gastroenterology, vol. 96, 199–207, 1999). According to the above guidelines for therapeutic trials, it is indicated that the diagnosis about an occurrence should be carried out based on an invasive test method, namely culture of a biopsy specimen from a gastric site, microscopy and a urease test, and that the judgment about bacterial eradication essentially requires culture of a biopsy specimen from a gastric site and microscopy and a urea breath test, which is a noninvasive test method. In special cases, for example in the case of a pediatric subject, it is indicated that the judgment should be carried out based on the combination of a test for anti-*Helicobacter pylori* antibodies in blood and the diagnosis about an occurrence.

However, these test methods for *Helicobacter pylori* infection have the following problems. The invasive test method inflicts a great deal of pain on subjects on the occasions of gastroscope insertion and biopsying. As for the noninvasive test methods, the pain sensation in subjects is markedly reduced but the urea breath test requires fasting prior to the test. Further, in carrying out the urea breath test, such apparatus as a mass spectrometer, an infrared spectrophotometer, etc. are required, hence the test can be carried out only in special institutions, and the resulting high cost is also a drawback. The antibody test is not suited for the judgment about bacterial eradication since the antibody titer in blood remains at high levels for a long term after eradication of the bacteria. Therefore, the advent of a noninvasive test method which may replace the above test methods and by which *Helicobacter pylori* infection can be detected directly and specifically with high accuracy has been awaited.

In the art, isolation culture of infective bacteria from digestive tract excreta, particularly feces, using a selection medium, has been made as a direct test method for infective bacteria in the digestive tract. As far as *Helicobacter pylori* is concerned, however, in spite of a large number of trials, there are few reports about the isolation, by culture, from feces. The reason may be considered that this microorganism has already undergone a transformation to the coccoid form, which cannot be culturally isolated, in the lower digestive tract since *Helicobacter pylori* undergoes, in vitro, a morphological change from the ordinary helical form to the coccoid form, which cannot be cultured, under unfavorable environmental conditions such as low temperature, nutritional deficiency and oxygen deficiency.

On the other hand, as regards direct detection of *Helicobacter pylori* from feces by an immunological method based on the antigen-antibody reaction, there is a report about the detection of *Helicobacter pylori* in excreta specimens, such as feces, by an immunoassay using polyclonal antibodies against *Helicobacter pylori* (J. Clin. Microbiol., vol. 33, 2162–2165, 1995; Japanese Kokai Publication Hei-10-10128 (JP 3043999)).

However, polyclonal antibodies generally have cross reactivity and are inferior in specificity and, in addition, are disadvantageous in that the antibody titer and specificity may vary depending on the lot of antiserum. Therefore, there is a problem that the production of diagnostic tests in which polyclonal antibodies are used is essentially difficult in terms of the quality control. In actuality, as regards the kit "HpSA" for detecting the antigen of *Helicobacter pylori* in feces, which is a product of Meridian, the patentee of JP No. 3043999, and in which a polyclonal antibody is used, questions about encountered false positive cases and low specificity have been raised (Medical Tribune, 4–5, Jun. 3, 1999 issue; Am. J. Gastroenterol., vol. 94, 1830–1833, 1999).

On the contrary, in Japanese Kokai Publication Hei-10-10128, it is described to the effect that since strains of *Helicobacter pylori* are susceptible to mutation, monoclonal antibodies capable of reacting only with respective individual antigens are not suited for use in detecting *Helicobacter pylori* but polyclonal antibodies, which can react with various antigens or epitopes, are rather suited for the detection of *Helicobacter pylori*.

SUMMARY OF THE INVENTION

In view of the above state of the art, it is an object of the present invention to provide a diagnostic method by which *Helicobacter pylori* infection can be diagnosed at low cost without causing pain on subjects and without requiring particular equipment and which is free of cross reactivity and excellent in specificity without variation among lots as a result of the use of a single antibody facilitating the quality control and which shows good sensitivity even when a single monoclonal antibody is used.

The present invention provides a monoclonal antibody which recognizes *Helicobacter pylori* catalase as an antigen.

The invention provides a hybridoma which produces a monoclonal antibody recognizing *Helicobacter pylori* catalase as an antigen.

The hybridoma of the invention is preferably 21G2 (FERM BP-7336), 41A5 (FERM BP-7337) or 82B9 (FERN BP-1338).

A monoclonal antibody which is produced by the hybridoma of the invention constitutes an aspect of the present invention.

An immunological assay method which is carried out using at least one monoclonal antibody species of the present invention also constitutes an aspect of the invention.

The immunological assay method of the invention is preferably carried out using any one of the monoclonal antibody species mentioned above.

The immunological assay method of the invention is preferably used for making judgment about *Helicobacter pylori* infection.

A specimen for the immunological assay method of the invention is preferably digestive tract excreta.

The immunological assay method of the invention is preferably carried out by an ELISA or immunochromatography technique.

A diagnosis kit which comprises at least one monoclonal antibody species of the invention also constitutes an aspect of the present invention.

The diagnosis kit of the invention preferably comprises any one of the above monoclonal antibody species.

The diagnosis kit of the invention is preferably used for making judgment about *Helicobacter pylori* infection.

A specimen for the diagnosis kit of the invention is preferably digestive tract excreta.

The diagnosis kit of the invention is preferably carried out by an ELISA or immunochromatography technique.

Catalase so referred to herein does not contain those proteins which correspond to subunits resulting from denaturation, dissociation or steric structure disentanglement by means of a denaturing agent such as SDS.

DETAILED DESCRIPTION OF THE INVENTION

Figure 1:
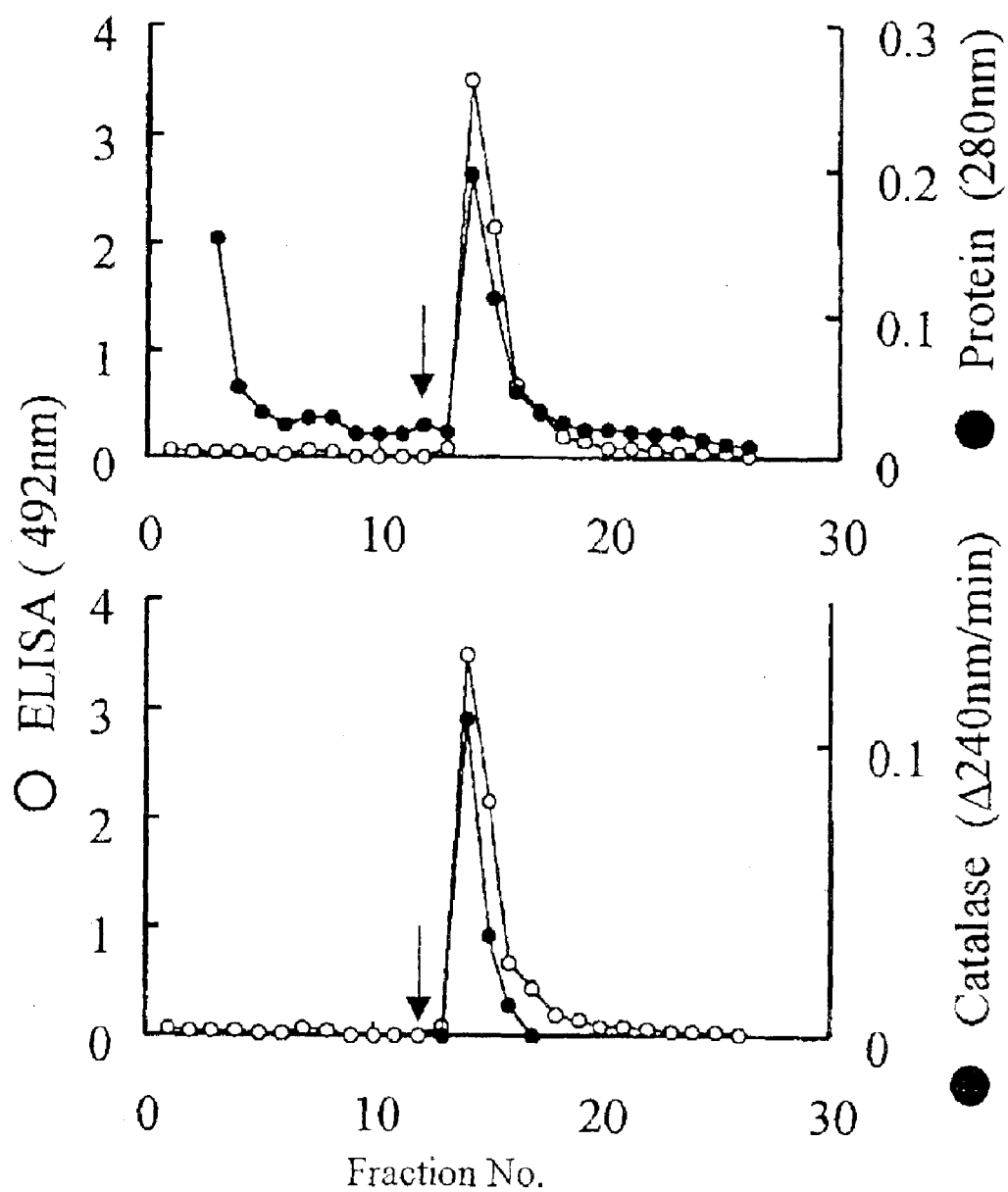
FIG. 1 illustrates the elution pattern in affinity chromatography as observed in Example 9.

In the following, the present invention is described in detail.

The monoclonal antibody of the present invention recognizes *Helicobacter pylori* catalase as an antigen.

The monoclonal antibody of the invention can be produced by the hybridoma according to the invention and thus can be obtainable, for example, by the culture fluid resulting from cultivating the hybridoma of the invention. However, the method of producing the monoclonal antibodies of the invention is not particularly restricted but a genetically engineered one, for instance, falls within the scope of the present invention if it can specifically bind to *Helicobacter pylori* catalase.

The hybridoma of the invention produces a monoclonal antibody recognizing *Helicobacter pylori* catalase as an antigen and can be obtained by subjecting spleen cells or lymph node cells of an animal immunized with *Helicobacter pylori* to cell fusion with myeloma cells.

The hybridoma of the present invention can be produced by a cell fusion technique known in the art. Thus, an animal other than human is immunized with *Helicobacter pylori* as an immunogen, hybridomas are produced by causing spleen cells or lymph node cells of that animal to fuse with myeloma cells, and a hybridoma producing a monoclonal antibody recognizing *Helicobacter pylori* is selected therefrom, whereby the hybridoma of the invention can be obtained.

The above-mentioned immunogen is not particularly restricted but may be any one containing *Helicobacter pylori* catalase. Thus, for example, there may be mentioned, cultures obtainable by cultivating a strain of *Helicobacter pylori* on an appropriate medium, cells in helical form, cells in coccoid form, disruption products, lysis products, or extraction products of such cells, and fractions thereof. The cells mentioned above may be dead cells or viable cells.

The above catalase is not particularly restricted but may be, for example, one deactivated, one having a partially destroyed steric structure or one resulting from partial deletion. Preferred are, however, ones having four subunits, more preferably native ones.

The term "native enzyme" as used herein denotes one retaining the intrinsic structure found under approximately physiological conditions and thus having all the subunits and the activity.

Among the immunogens mentioned above, a disruption product of coccoid cells is preferred. Since, in vitro, *Helicobacter pylori* morphologically changes from the ordinary helical form to a coccoid form, which cannot be cultured, in unfavorable environmental conditions such as low temperature, nutritional deficiency, oxygen deficiency and the like, it is considered that it has been transformed into coccoid form, which cannot be culturally isolated, in the digestive tract excreta as well. It is also considered that cells of *Helicobacter pylori* occur in a disrupted condition in the lower digestive tract.

The strain of *Helicobacter pylori* to be used as the above-mentioned immunogen is not particularly restricted but includes, for example, the strains ATCC 43504 and NCTC 11638, which are standard strains, and other strains isolated from infected persons. The genetic type of *Helicobacter pylori* to be used as the above immunogen is not particularly restricted. Thus, for example, it may have or may not have vacA or cagA and, further, vacA may have any of the sequences S1a, S1b and S2 and may have any of the sequences m1 and m2.

The animal to be immunized for producing the hydridomas of the invention is not particularly restricted but includes, for example, goats, sheep, guinea pigs, mice, rats, and rabbits. Among them, mice are preferred.

The above animals to be immunized can be immunized by any method known in the art. In immunizing mice, for instance, there may be mentioned the method comprising emulsifying 1 to 100 μg, preferably 50 to 100 μg, per dose, of the antigen for immunization in an equal volume (0.1 mL) of physiological saline and Freund's complete adjuvant or RIBI adjuvant system and administering the emulsion to the above animals to be immunized subcutaneously at a dorsal or abdominal site or intraperitoneally 3 to 6 times at intervals of 2 to 3 weeks.

In the practice of the present invention, after immunization of the above animals to be immunized, individuals high in antibody titer are selected, the spleen or lymph node of each of them is excised 3 to 5 days after the final booster, and antibody-producing cells contained in such tissue can be fused with myeloma cells by a cell fusion method known in the art in the presence of a fusion promoter.

The above fusion promoter is not particularly restricted but includes, for example, polyethylene glycol (hereinafter referred to as "PEG"), Sendai virus and so forth. PEG is preferred, however.

The above-mentioned myeloma cells are not particularly restricted but include, for example, mouse-derived cells, such as P3U1, NS-1 and P3×63.Ag8.653 cells; and rat-derived cells, such as AG1 and AG2 cells.

The above cell fusion method is not particularly restricted but may include, for example, the method comprising mixing spleen cells with myeloma cells in a ratio of 1:1 to 10:1, adding PEG having a molecular weight of 1,000 to 6,000 thereto to a concentration of 10 to 80% and incubating the mixture at 20 to 37° C., preferably 30 to 37° C., for 3 to 10 minutes.

In the practice of the invention, the selection of hybridomas which produces a monoclonal antibody recognizing

*Helicobacter pylori* can be made, for example, by cultivating them on a selection medium, such as HAT medium, on which the hybridomas alone can grow, and measuring the antibody activity in each hybridoma culture supernatant by such a method as enzyme-linked immunosorbent assay (ELISA). Furthermore, in the present invention, the establishment of a hybridoma, which produces a monoclonal antibody recognizing *Helicobacter pylori*, can be realized, for example, by subjecting the hybridoma which produces a monoclonal antibody recognizing *Helicobacter pylori* to repeated cloning by such a method as limiting dilution.

As the hybridoma of the present invention, there may be mentioned, for example, 21G2 (deposition number FERM BP-7336), 41A5 (deposition number FERM BP-7337), and 82B9 (deposition number FERM BP-7338). These hybridomas have been deposited, as of Oct. 14, 1999, with National Institute of Bioscience and Human-Technology, Agency of Industrial Science and Technology (1–3 Higashi 1-chome, Tsukuba-shi, Ibaraki-ken, Japan).

The method of preparing the monoclonal antibody of the invention in large quantities is not particularly restricted but may be, for example, the method comprising transplanting the hybridoma into the abdominal cavity of mice administered in advance with pristane, recovering the ascitic fluid and obtaining the antibody from the same. The monoclonal antibody of the invention in ascitic fluid can be purified, for example, by a method known in the art using a protein A or protein G column, etc.

The monoclonal antibody of the invention recognizes catalase as an antigen.

The above catalase is not particularly restricted but may be any one retaining the epitope. For example, it may be one deactivated, one having a partially destroyed steric structure, or one resulting from partial deletion. One having four subunits is preferred, however, and a native one is more preferred. The above-mentioned catalase includes those having a mutation or the like.

The strain of *Helicobacter pylori*, which produces the above-mentioned catalase, is not particularly restricted.

The genetic type of *Helicobacter pylori* which produces the above catalase is not particularly restricted, either. For example, it may have or may not have vacA or cagA, and, further, vacA may have any of the sequences S1a, S1b and S2 and may have any of the sequences m1 and m2.

The morphology of the above *Helicobacter pylori* which produces catalase is not particularly restricted but includes, for example, the helical form of *Helicobacter pylori* and the coccoid form of *Helicobacter pylori*.

The class and subclass of the monoclonal antibody of the invention are not particularly restricted but may be any of $IgG_1$, $IgG_2$, $IgG_3$, $IgG_4$, IgM, IgE, $IgA_1$, $IgA_2$ and IgD. The L chain is not particularly restricted, either, but may be the γ chain or κ chain.

The monoclonal antibody of the invention is not particularly restricted but may be any of those capable of specifically binding to *Helicobacter pylori* catalase. For example, it may be $F(ab')_2$, Fab' or Fab, which is a decomposition product of the monoclonal antibody of the invention, or a chimera antibody.

The above hybridoma strains 21G2 (deposition number FERM BP-7336), 41A5 (deposition number FERN BP-7337), and 82B9 (deposition number FERM BP-7338) produce respective monoclonal antibodies (hereinafter respectively sometimes referred to also as "monoclonal antibody 21G2", "monoclonal antibody 41A5", and "monoclonal antibody 82B9"), which recognize native catalase of *Helicobacter pylori*.

The present inventors carried out antibody-immobilized affinity chromatography of a *Helicobacter pylori* cell disruption product using the monoclonal antibody 21G2, monoclonal antibody 41A5 and monoclonal antibody 82B9, respectively, upon which a protein having a molecular weight of 270 kDa as contained in the disruption product of *Helicobacter pylori* cells was detected. Upon SDS-polyacrylamide gel electrophoresis of this protein, a single band showing a molecular weight of 59 kDa was detected. Upon sequencing, the N-terminal amino acid sequence of this protein agreed with the amino acid sequence of *Helicobacter pylori* catalase. It is known that *Helicobacter pylori* catalase has a molecular weight of 200 kDa and has a tetramer structure composed of 4 subunits each having a molecular weight of 50 kDa (J. Gen. Microbiol. (1991), 137, 57–61).

Therefore, base on the above results, the protein detected by the monoclonal antibody 21G2, monoclonal antibody 41A5 and monoclonal antibody 82B9 was identified as *Helicobacter pylori* catalase having four subunits and it was revealed that each of the above-mentioned monoclonal antibodies recognizes the catalase having four subunits.

Catalase activity assay revealed that the catalase detected in the above antibody-immobilized affinity chromatography had activity and that this catalase was the so-called native enzyme.

None of the monoclonal antibody 21G2, monoclonal antibody 41A5 and monoclonal antibody 82B9 reacted with the subunits of catalase resulting from dissociation.

The proportion of catalase to the whole protein in *Helicobacter pylori* cell is at most 0.5% on the weight basis as roughly calculated based on the increase in specific activity in the process of purification of catalase as described in J. Gen. Microbiol. (1991), 137, 57–61.

In view of this point, it is a surprising and quite unexpected finding that the monoclonal antibody 21G2, monoclonal antibody 41A5 and monoclonal antibody 82B9 can recognize catalase having four subunits.

Catalase has been very well conserved among different species and it is known that *Helicobacter pylori* catalase is highly homologous to other bacterial catalase species (J. Bacteriol. (1996), 178 (23), 6960–6967). However, as shown in Example 3, the monoclonal antibody 21G2, monoclonal antibody 41A5 and monoclonal antibody 82B9 did not react at all with catalase species derived from other bacterial species than *Helicobacter pylori*.

While it is also known that there exist various mutants of *Helicobacter pylori* (Molecular Microbiology (1996), 20, 833–842), the monoclonal antibody 21G2, monoclonal antibody 41A5 and monoclonal antibody 82B9 surprisingly reacted well with all *Helicobacter pylori* strains, as shown in Example 3.

In view of the fact that the monoclonal antibodies of the present invention react well with various mutants of *Helicobacter pylori*, the epitope which is recognized by the monoclonal antibodies of the invention seems to be a site well conserved among catalase species within mutants.

As will be mentioned below in detail, the monoclonal antibodies of the invention make it possible to make judgment about the occurrence or nonoccurrence of *Helicobacter pylori* infection with very high accuracy using feces as specimens.

Feces specimens were subjected to immunological assay using the monoclonal antibody 21G2, monoclonal antibody 41A5 and monoclonal antibody 82B9. The above monoclonal antibodies each reacted only with the feces of subjects infected with *Helicobacter pylori*. By this, it was revealed that *Helicobacter pylori* catalase having four subunits is present in the feces of subjects infected with *Helicobacter pylori*. It has been quite unknown in the art that the *Helicobacter pylori* catalase occurring in feces is not dissociated into each subunit but retains the four subunits. This is quite surprising in view of the fact that proteins are generally digested by proteases in the digestive tract.

A column was prepared by immobilizing the monoclonal antibody 21G2 thereon and affinity chromatography was carried out using, as samples feces from persons infected with *Helicobacter pylori*, and the eluate fractions were subjected to ELISA and catalase activity assay. The catalase activity was in agreement with the antigenicity.

In view of the foregoing, it was revealed that the feces of persons infected with *Helicobacter pylori* contain native catalase having four subunits and catalase activity. It has been quite unexpected that *Helicobacter pylori* catalase is not digested in the digestive tract but is excreted in the form of native enzyme having activity and thus occurs in feces.

In Japanese Kokai Publication Hei-09-322772 and Infect. Immun. (1997), 65, 4668–4674, there are disclosed monoclonal antibodies which react with a protein corresponding to each disentangled subunit obtainable by denaturation and dissociation of *Helicobacter pylori* catalase by SDS-PAGE. However, it is not clear whether these monoclonal antibodies react with native catalase retaining the steric structure and having activity or whether they can detect *Helicobacter pylori* in excreta specimens, such as feces.

On the contrary, the monoclonal antibody of the present invention makes it possible to recognize the occurrence or nonoccurrence of *Helicobacter pylori* infection using digestive tract excreta, such as feces, which can be collected with ease, as specimens.

The field of application of the monoclonal antibody of he present invention is not particularly restricted but can be used, in immunological assays, for making judgment about *Helicobacter pylori* infection.

The immunological assay method of the present invention is carried out using at least one monoclonal antibody species according to the invention, and the method can be carried out using only one species.

Generally, as the monoclonal antibody used in the immunological assay method, monoclonal antibodies, which are superior in sensitivity, is considered as preferred because of higher specificity and lower background noise compared with polyclonal antibodies, which are low in specificity and high in background noise.

It is known, however, that there are various mutants of *Helicobacter pylori*. Therefore, it has been considered that it would be very difficult to detect the infection or occurrence using a single monoclonal antibody. As described in Japanese Kokai Publication Hei-10-10128, there is also an opinion that polyclonal antibodies, which can react with a variety of antigens, are more suited for the detection of infection with or occurrence of a bacterial species having a variety of antigens. Further, a method of detecting *Helicobacter pylori* using a plurality of monoclonal antibodies has been disclosed (WO 00/26671). However, any method has not yet been developed for detecting *Helicobacter pylori* using a single monoclonal antibody.

On the contrary, it has surprisingly been found that the monoclonal antibody of the present invention can detect *Helicobacter pylori* with very high accuracy using a single antibody species.

The monoclonal antibodies described in WO 00/26671 recognize urease, heat shock proteins, alkaline hydroperoxidase reductase, 20 kDa protein (3-dehydrokinase type 2), 16.9 kDa protein (neutrophile activating protein) and 33.8 kDa protein (fructose-bisphosphatase aldolase) as antigens. Catalase is not mentioned at all. The assay method described in WO 00/26671 is not satisfactory in detection sensitivity.

As the immunological assay method of the present invention, there may be mentioned, for example, enzyme immunoassay (EIA), enzyme-linked immunosorbent assay (ELISA), radioimmunoassay (RIA), fluorescence immunoassay (FIA), western blotting, immunochromatography and like techniques. The various immunological assay methods mentioned above can be used in assaying the target antigens or antibodies by using an antigen or antibody labeled with a labeling agent in the manner of competitive or sandwich method, etc.

Among the above-mentioned various immunological assay methods, ELISA and immunochromatography techniques are preferred.

The above competitive method is based, for example, on the quantitatively competitive binding reaction of *Helicobacter pylori* catalase in a test specimen and a known amount of labeled *Helicobacter pylori* catalase to the monoclonal antibody of the present invention. In the competitive method specifically mentioned above, a predetermined amount of the antibody immobilized on a carrier and a predetermined amount of *Helicobacter pylori* catalase labeled with a labeling agent are added to a specimen solution containing *Helicobacter pylori* catalase. Then, the activity of the labeling agent retained on the carrier or of the labeling agent not retained on the carrier is determined. In this case, it is preferable to add the antibody and labeled antigen almost simultaneously.

The above-mentioned sandwich method comprises, for example, sandwiching *Helicobacter pylori* catalase in a specimen between the immobilized monoclonal antibody of the invention and the monoclonal antibody of the invention labeled with a labeling agent, and then adding a substrate or the like against the labeling agent such as an enzyme, to cause color development or the like, and thereby detect *Helicobacter pylori* catalase in the specimen.

As the above labeling agent, there may be mentioned radioisotopes (hereinafter abbreviated as "RI") such as $^{125}$I, enzymes, enzyme substrates, luminescent substances, fluorescent substances, biotin, and colored substances. In binding these labeling agents to the antigen or antibody, the maleimide method [J. Biochem. (1976), 79, 233], activated biotin method [J. Am. Chem. Soc. (1978), 100, 3585] or hydrophobic bond method, for instance, can be used.

As the enzyme mentioned above, there may be mentioned, for example, peroxidase, alkaline phosphatase, β-galactosidase, and glucose oxidase. As for the substrate to be used on that occasion, one suitable for the enzyme employed may be selected and there may be mentioned, for example, ABTS, luminol-$H_2O_2$, o-phenylenediamine-$H_2O_2$ (against peroxidase), p-nitrophenyl phosphate, methylumbelliferyl phosphate, 3-(2'-spiroadamantan)-4-methoxy-4-(3"-phosphoryloxy)phenyl-1,2-dioxetane (against alkaline phosphatase), p-nitrophenyl-β-D-galactose, and methylumbelliferyl-β-D-galactose (against β-galactosidase).

The above assay can be carried out by allowing the reaction to proceed at 4 to 40° C. for 1 minute to 18 hours and then measuring the resulting developed color or amount of fluorescence, luminescence, or coloration. Alternatively, the so-called rate assay may be employed which is carried out while incubating in the range of 4 to 40° C.

The radiolabeling to the above antigen or antibody can easily be carried out using the Bolton-Hunter reagent, which is commercially available. For example, it can be carried out by adding the Bolton-Hunter reagent to a solution prepared by dissolving an antigen or antibody in 0.1 M aqueous solution of sodium hydrogen carbonate and, after the lapse of 1 to 2 hours, removing the unreacted portion of the Bolton-Hunter reagent using a G-25 desalting column or the like.

In addition, the radiolabeling with $^{125}$I can be easily carried out by employing the chloramine T method, the iodogen method or the like.

As the above luminescent substance, there may be mentioned, for example, isoluminol and acridine esters and, as the above fluorescent substance, there may be mentioned, for example, fluorescein and rhodamine. In this case, the labeling can be carried out with ease by employing the activated ester method or the isocyanate method ("Enzyme immunoassay techniques", published in 1987 by Igaku Shoin). As the above colored substance, there may be mentioned, for example, colored latex particles and colloidal gold.

For carrying out the immunological assay method of the present invention by the above-mentioned competitive method, a specimen containing an unknown amount of *Helicobacter pylori* catalase, for instance, is added to a solid phase to which the monoclonal antibody of the present invention is bound physically or chemically by known means, and the reaction is allowed to proceed. Simultaneously, a predetermined amount of *Helicobacter pylori* catalase labeled with a labeling agent is added and the reaction is allowed to proceed.

In carrying out the immunological assay method of the present invention by the above-mentioned sandwich method, a specimen containing an unknown amount of *Helicobacter pylori* catalase, for instance, is added to a solid phase to which the monoclonal antibody of the present invention is bound physically or chemically by known means, and the reaction is allowed to proceed. Thereafter, the monoclonal antibody of the invention labeled with a labeling agent is added and the reaction is allowed to proceed.

Then, in both cases, the solid phase is thoroughly washed, if necessary, and the activity of the labeling agent bound to the solid phase is measured. When the above labeling agent is R1, the measurement is carried out using a well counter or a liquid scintillation counter. When the labeling agent is an enzyme, the substrate is added and, after standing, the enzyme activity is measured by colorimetry or fluorometry. When the labeling agent is a fluorescent substance, luminescent substance or colored substance, the measurement can be made respectively by a method known in the art.

The immunological assay method of the present invention uses the monoclonal antibody of the present invention and therefore has outstanding characteristics, namely the epitope specifically occurring in *Helicobacter pylon* catalase can be recognized without erroneously detecting other substances as a result of a cross reaction and thus measurements can be carried out with very high specificity.

For carrying out the immunological assay method of the present invention, the diagnosis kit of the present invention can be used. The diagnosis kit of the invention comprises at least one monoclonal antibody species of the invention and may comprise only one monoclonal antibody species. The monoclonal antibody of the invention, which is to be used in the diagnosis kit of the invention, is not particularly restricted but may be any of those recognizing *Helicobacter pylori* catalase, and may be the decomposition products of the monoclonal antibody of the invention such as F(ab')$_2$, Fab', Fab and the like.

The diagnosis kit of the invention can immunologically detect the occurrence of *Helicobacter pylori* cells or of *Helicobacter pylori* catalase and therefore makes judgment about *Helicobacter pylori* infection.

In the diagnosis kit of the invention, the monoclonal antibody of the invention may be immobilized on a solid phase in advance, and the monoclonal antibody of the invention may be labeled with the above-mentioned labeling agent in advance.

The solid phase to be used in the diagnosis kit of the invention is not particularly restricted but includes, for example, polymers such as polystyrene, glass beads, magnetic particles, microplates, filter paper for immunochromatography, glass filters and other insoluble carriers.

The diagnosis kit of the invention may further comprise other constituents.

The other constituents mentioned above are not particularly restricted but include, for example, enzymes for labeling, substrates therefor, radioisotopes, luminescent substances, fluorescent substances, colored substances, buffer solutions, and plates, and those mentioned hereinabove can be used as these.

Although the form of the diagnosis kit of the invention is not particularly restricted, but integrated type diagnosis kit comprising the constituents of the diagnosis kit of the invention together is preferred in order to carry out the diagnosis in a rapid, simple and easy manner.

The above integrated type diagnosis kit is not particularly restricted but may be of the cassette type, cartridge type, or the like.

As an embodiment of the above-mentioned cassette type, there may be mentioned, for example, an embodiment which comprises, using a immunochromatography technique, a reaction cassette, a membrane contained therein, the monoclonal antibody of the invention immobilized on said membrane at one end thereof (downstream side), a developing solution provided on the membrane at the opposite end thereof (upstream side), a pad containing a substrate against the above-mentioned labeling agent and disposed in the vicinity of the developing solution on the side downstream side thereof, and a pad containing the monoclonal antibody of the invention labeled with the above-mentioned labeling agent and disposed in the middle portion of the membrane.

In using the diagnosis kit having the embodiment of the cassette type mentioned above by way of example, the specimen is applied onto the pad containing the monoclonal antibody of the invention labeled with the above labeling agent and, after allowing the formation of the bonding product between *Helicobacter pylori* catalase contained in the specimen and the monoclonal antibody of the invention labeled with the labeling agent, the above-mentioned developing solution is allowed to develop to thereby transfer the bonding product formed to the site in which the monoclonal antibody of the invention is immobilized, where the complex of *Helicobacter pylori* catalase, the monoclonal antibody of the invention labeled with the labeling agent and the immobilized monoclonal antibody of the invention is formed. Then, the above-mentioned labeling agent reacts with the above-mentioned substrate to develop a color or the like. This developed color or the like is measured, whereby judgment about *Helicobacter pylori* infection can be made.

In cases where an embodiment comprising diluting the specimen using a sufficient amount of a developing solution and dropping the resulting solution onto the membrane is empolyed, it is not necessary to provide the developing solution on the membrane in advance. When a colored substance such as colored latex particles is used as the above-mentioned labeling agent, no substrate is required and whether the above-mentioned complex is formed or not at the site in which the monoclonal antibody of the invention is immobilized can be judged based on the coloration due to the colored substance.

As an embodiment of the above-mentioned cartridge type for carrying out the reaction by the above-mentioned competitive method, for instance, there may be mentioned a cartridge or the like having a plurality of wells, which are integrally formed, and comprising (a) a well containing the monoclonal antibody of the invention, (b) a well containing a liquid reagent (e.g. buffer solution) containing *Helico-* bacter pylori labeled with the above-mentioned labeling agent, and (c) a well containing a liquid reagent (e.g. buffer solution) containing a substrate against the above-mentioned labeling agent and, for carrying out the reaction by the sandwich method, there may be mentioned a cartridge or the like having a plurality of wells, which are integrally formed, and comprising (a) a well containing a insoluble carrier on which the monoclonal antibody of the invention is immobilized, (b) a well containing a liquid reagent (e.g. buffer solution) containing the monoclonal antibody of the invention labeled with the above-mentioned labeling agent, and (c) a well containing a liquid reagent (e.g. buffer solution) containing a substrate against the above-mentioned labeling agent.

In using the cartridge type diagnosis kit of the present invention mentioned above by way of example, the reaction and assay can generally be carried out in the same manner as in carrying out the competitive or sandwich method.

The diagnosis kit of the invention may be one for carrying out the above-mentioned competitive method or the above-mentioned sandwich method. One for carrying out the sandwich method is preferred, however. The above sandwich method has advantages, namely it is high in sensitivity, requires a short reaction time, and is superior in accuracy. By using immunochromatography technique as the above sandwich method, it becomes possible to produce a kit which renders the test procedure easy and simple and with which the judgment of the results can easily be done by visual observation. When the above sandwich method is used in the manner of ELISA technique, the enzyme reaction product is formed depending on the amount of the assay target substance and therefore a system by which the color development or the like in the case of positive *Helicobacter pylori* infection can be confirmed by visual observation can easily be established.

The specimen to be used with the diagnosis kit of the present invention is not particularly restricted but includes, for example, gastric contents, gastric washings, and digestive tract excreta. Digestive tract excreta, such as feces, are preferred, however, since they can easily be collected without imposing any burden on subjects.

The diagnosis kit of the present invention may be used for examining for the occurrence or nonoccurrence of the infection prior to bacterial eradication treatment and/or for making judgment about the success or failure thereof after bacterial eradication treatment.

The diagnosis kit of the present invention has a high level of detection sensitivity and produces no false negative or false positive problems, without any difference among lots since it uses a monoclonal antibody.

In accordance with the present invention, the influences of other substances occurring in the specimen can be eliminated by using the monoclonal antibody recognizing *Helicobacter pylori* catalase as an antigen, so that the occurrence of *Helicobacter pylori* can be detected with very high sensitivity and specificity. Since the hybridoma which produces a monoclonal antibody against *Helicobacter pylori* catalase have been established, it is now possible to produce the same monoclonal antibody almost semi-permanently. The diagnosis kit in which the monoclonal antibody of the present invention is used can use digestive tract excreta as specimens, so that *Helicobacter pylori* infection can be detected in a simple and easy manner and efficiently without causing any pain on subjects. Further, in cases where only one monoclonal antibody species is used, the diagnosis kit of the invention in which the monoclonal antibody of the present invention is used can stably attain very high accuracy without any difference among lots, hence can detect *Helicobacter pylori* infection always specifically and with great accuracy. The above diagnosis kit is easy in carrying out the assay and is very useful at the site of medical care.

BEST MODES FOR CARRYING OUT THE INVENTION

The following examples and test examples illustrate the present invention in further detail. They are, however, by no means limitative of the scope of the present invention.

EXAMPLE 1

[Monoclonal Antibody Production]

(1) Preparation of a *Helicobacter pylori* Coccoid Cell Suspension (Immunogen)

Brain heart infusion agar medium (product of Difco) supplemented with 5% equine defibrinated blood was streaked with *Helicobacter pylori* (ATCC 43504) in series. The plate was incubated at 37° C. for 3 to 4 days in a microaerobic environment and then further incubated at 37° C. for 7 days in an anaerobic environment to cause the cells to become coccoid. Each colony obtained was scraped off with a platinum loop or the like and suspended in phosphate-buffered physiological saline (PBS). *Helicobacter pylori* cells were collected by 10 minutes of centrifugation at 10,000×g at 4° C. and suspended in 0.5 % formalin, and the suspension was allowed to stand at 4° C. for 4 days for inactivation. Thereafter, the cells were washed by three repetitions of the procedure comprising suspending in PBS followed by 10 minutes of centrifugation at 10,000×g at 4° C. and then suspended in PBS.

(2) Preparation of a Disruption Product of *Helicobacter pylori* Coccoid Cells (Immunogen)

The cell suspension obtained in (1) was disrupted by 10 minutes of ultrasonication using an ultrasonic disrupter (product of Seiko Denshi Kogyo, Model 7250) under output 3.50% duty cycle conditions.

(3) Immunization and Cell Fusion

Equal amounts of the immunogen prepared as described under (1) or (2) (*Helicobacter pylori* coccoid cell suspension or the disruption product of *Helicobacter pylori* cells) and Freund's complete adjuvant (product of Calbiochem) were mixed up to give an oil emulsion. This emulsion was subcutaneously administered to BALB/cA mice (products of CLEA Japan, 6-week-old, males) at a dorsal site at a dose of 0.2 mL. Booster was carried out 7 days and 14 days after the first immunization and, further, 3 days prior to cell fusion, 0.2 mL of the above immunogen was intraperitoneally administered. Three days after the final booster, the spleen cells were excised from each mouse and mixed with myeloma cells (P3×63.Ag8.653 strain, RCB 0146, Riken Gene Bank) in a ratio of 10:1 and fused together using 50% polyethylene glycol 4000. Hybridomas were cultured selectively on HAT medium (product of Gibco).

(4) Hybridoma Selection

On the 12th day after cell fusion, the antibody activity in each culture supernatant was measured by ELISA. The culture supernatant of fusion cells, 200-μl each, was added to wells of a 96-well ELISA plate (product of Coaster) with 10 μg/mL of the immunogen immobilized thereon and, after allowing the reaction to proceed at 37° C. for 1 hour and washing with 0.05% Tween 20-containing PBS (washing solution), 200 μL of peroxidase-labeled anti-mouse IgG (product of Cappel, 1:20,000) was added to each well. After allowing the reaction to proceed at 37° C. for 1 hour, the plate was washed with the above washing solution.

Thereafter, 200 μL of a substrate solution (0.1 M o-phenylenediamine and 0.012% aqueous hydrogen peroxide) was added to each well and the reaction was allowed to proceed at room temperature for 15 minutes. Thereafter, the enzyme reaction was terminated by adding 50 μL of 3.5 N sulfuric acid to each well, and the absorbance at 492 nm was measured. Those hybridomas clones which produced an antibody reactive with the above immunogen and gave an absorbance not lower than 0.15 were selected.

Each clone was subjected to two repetitions of cloning by the limiting dilution method. Hybridomas after cloning were transplanted into BALB/cA mice and, as a result, 32 hybridoma clones were found to produce respective monoclonal antibodies that can be recovered as ascitic fluids.

EXAMPLE 2

[Selection of Monoclonal Antibodies Specifically Recognizing *Helicobacter pylori* in Digestive Tract Excreta by Sandwich ELISA]

(1) Preparation of Monoclonal Antibody-Immobilized Plates

Each 1-mL portion of the ascetic fluids of the 32 clones was diluted two-fold with PBS, 2 mL of saturated ammonium sulfate was added dropwise, and the mixture was allowed to stand at 4° C. for 4 hours. Then, the mixture was centrifuged at 3000 rpm for 20 minutes, and the sediment was suspended in 2 mL of PBS and dialyzed. These monoclonal antibodies were immobilized on 96-well ELISA plates in the following manner. Thus, each monoclonal antibody was diluted to 5 µg/mL and 0.2 mL of the dilution was added to each well of 96-well ELISA plates. After overnight standing at 4° C., the plates were washed with PBS, then 0.25 mL of 1% skim milk-PBS was added to each well and the plates were allowed to stand at 4° C. for 1 hour for blocking. Thereafter, the plates were washed with the above washing solution.

(2) Preparation of Biotin-Labeled Monoclonal Antibodies

Each 3-mg portion of the 32-clone monoclonal antibodies prepared in (1) was mixed with 10 mg of biotinyl N-hydroxysuccinimide ester (product of Zymed) and the reaction was carried out in 0.1 M sodium hydrogen carbonate (pH 8) with stirring at room temperature for 3 hours. The reaction mixture was dialyzed overnight against 5 L of PBS at 4° C. to give the biotin-labeled monoclonal antibody.

(3) Selection of Monoclonal Antibodies Specifically recognizing *Helicobacter pylori* in digestive tract excreta Feces specimens, 250 mg each, from one person judged as *Helicobacter pylori* positive and one person judged as negative by the urea breath test were each suspended in 0.5 mL of 0.1% skim milk-PBS, each mixture was centrifuged at 3,000 rpm for 10 minutes, and the supernatant thus separated was used as a fecal extract. 0.2 mL of each fecal extract was added to each well of the monoclonal antibody-immobilized plate prepared as described in (1). After 1 hour of standing at 37° C., the plate was washed with 5 portions of the above washing solution, and 0.2 mL of each biotin-labeled monoclonal antibody prepared in (2) was added. After 1 hour of standing at 37° C., the plate was washed with she above washing solution, and 0.2 mL of peroxidase-labeled avidin (product of Zymed) was added. After 1 hour of standing at 37° C., the plate was washed with the above washing solution, 0.2 mL of a substrate solution (0.1 M o-phenylenediamine and 0.012% aqueous hydrogen peroxide) was added to each well, and the reaction was allowed to proceed at room temperature for 10 minutes. Thereafter, the enzyme reaction was terminated by adding 50 µL of 3.5 N sulfuric acid, and the absorbance was measured at 492 nm. As shown in Table 1, sandwich ELISA in which three monoclonal antibodies, 21G2, 41A5 and 82B9, used singly or in combination, were found to show high reactivity against the fecal specimen of the person infected with *Helicobacter pylori*.

TABLE 1

| Combination of monoclonal antibodies | | Absorbance | |
|---|---|---|---|
| Immobilized | Label | Positive subject | Negative subject |
| 21G2 | 21G2 | 3.3 | 0.043 |
| 21G2 | 41A5 | >3.5 | 0.075 |
| 21G2 | 82B9 | >3.5 | 0.067 |
| 41A5 | 41A5 | 3.3 | 0.10 |
| 41A5 | 21G2 | >3.5 | 0.080 |
| 41A5 | 82B9 | >3.5 | 0.035 |
| 82B9 | 82B9 | >3.5 | 0.071 |
| 82B9 | 21G2 | 3.3 | 0.066 |
| 82B9 | 41A5 | >3.5 | 0.064 |

The hybridomas producing the respective monoclonal antibodies have been deposited with the National Institute of Bioscience and Human-Technology, Agency of Industrial Science and Technology under the designations hybridoma 21G2 (FERM BP-7336), hybridoma 41A5 (FERM BP-7337) and hybridoma 82B9 (FERM BP-7338). The immunoglobulin subclass of each monoclonal antibody was checked using an immunoglobulin typing kit mouse (product of Wako Pure Chemical Industries), and as a result, all the three clones were found to belong to $IgG_1$ with κ type L chains.

EXAMPLE 3

[Reactivity Comparison Among Strains and Reactivity with Other Bacterial Species]

(1) Preparation of *Helicobacter pylori* Cell Suspensions

Brain heart infusion agar medium supplemented with 5% equine defibrinated blood was streaked with each of *Helicobacter pylori* strains (ATCC 43504; Tokai University Hospital clinical isolates No. 130 and No. 112; Hyogo Medical College clinical isolates No. 526, No. 4484, No. 5017, No. 5025, No. 5049, No. 5142, No. 5287, No. 5308, No. 5314 and No. 5330) in series. The plates were incubated at 37° C. under microaerobic conditions for 3 to 4 days to give colonies of helical cells, or further allowed to stand a: 37° C. for 7 days in an anaerobic environment to give colonies of coccoid cells. Each colony was scraped off with a platinum loop or the like and suspended in PBS. Cells were collected by 10 minutes of centrifugation at 10,000×g at 4° C. and suspended in 0.5% formalin, and the suspension was allowed to stand at 4° C. for 4 days for inactivation. Thereafter, the cells were washed by three repetitions of the procedure comprising suspending in PBS, followed by 10 minutes of centrifugation at 10,000×g at 4° C., and then again suspended in PBS. Thus were obtained *Helicobacter pylori* helical cell suspensions and coccoid cell suspensions.

(2) Preparation of Human Enterobacterial and Campylobacter Jejuni Cell Suspensions Typical bacterial species isolable from human feces, namely two enterobacterial species *Bacteroides vulgatus* and *Escherichia coli*, and the helical bacterial species *Campylobacter jejuni* were cultured in the manner mentioned below and, from the colonies obtained, each cell suspension was prepared in the same manner as mentioned in (1). Thus, *Bacteroides vulgatus* (IFO 14291) was anaerobically cultured on BL agar medium (product of Nissui Pharmaceutical) supplemented with 5% equine defibrinated blood at 37° C. for 2 days. *Escherichia coli* (ATCC 25922) was aerobically cultured on brain heart infusion agar medium at 37° C. for 1 day. *Campylobacter jejuni* (80068, Tokai University Hospital clinical isolate) was microaerobically cultured on brain heart infusion agar medium supplemented with 5% equine defibrinated blood at 37° C. for 2 days.

(3) Preparation of Cell Suspensions of Other *Helicobacter* Species *Helicobacter felis* (ATCC 49179) and *Helicobacter hepaticus* (ATCC 51448) were cultured on brain heart infusion agar medium supplemented with 5% equine defibrinated blood in the same manner as in (1) and, from the thus-obtained colonies of helical cells, helical cell suspensions were obtained in the same manner as in (1).

(4) Preparation of Cell Disruption Products

Each cell suspension obtained in (1), (2) or (3) was subjected to ultrasonication for cell disruption using an ultrasonic disrupter (product of Seiko Denshi Kogyo, Model 7250) under output 3.50% duty cycle conditions.

(5) Sandwich ELISA

Each cell disruption product obtained in (4) (0.2 mL; protein concentration 10 μg/mL) was subjected to sandwich ELISA by the method of Example 2 (3) (monoclonal antibody 41A5-immobilized plate: biotin-labeled monoclonal antibody 82B9, monoclonal antibody 21G2-immobilized plate: biotin-labeled monoclonal antibody 41A5, monoclonal antibody 21G2-immobilized plate: biotin-labeled monoclonal antibody 82B9, monoclonal antibody 21G2-immbolized plate: biotin-labeled monoclonal antibody 21G2, and Meridian's product HpSA). The results are shown in Table 2.

TABLE 2

| Antibody | Immobilized monoclonal antibody | Absorbance | | | | |
|---|---|---|---|---|---|---|
| | | 21G2 | 41A5 | 21G2 | 21G2 | HpSA |
| | Labelled monoclonal antibody | 41A5 | 82B9 | 82B9 | 21G2 | |
| Antigen | *Helicobacter pylori* ATCC 43504 helical cells | >3.5 | >3.5 | >3.5 | >3.5 | >3.5 |
| | *Helicobacter pylori* ATCC 43504 spherical cells | >3.5 | >3.5 | >3.5 | — | — |
| | *Helicobacter pylori* No. 130 helical cells | >3.5 | >3.5 | >3.5 | — | — |
| | *Helicobacter pylori* No. 130 spherical cells | >3.5 | >3.5 | >3.5 | — | — |
| | *Helicobacter pylori* No. 112 helical cells | >3.5 | >3.5 | >3.5 | — | — |
| | *Helicobacter pylori* No. 112 spherical cells | >3.5 | >3.5 | >3.5 | — | — |
| | *Helicobacter pylori* No. 526 helical cells | — | — | — | >3.5 | — |
| | *Helicobacter pylori* No. 4484 helical cells | — | — | >3.5 | — | |
| | *Helicobacter pylori* No. 5017 helical cells | — | — | — | >3.5 | — |
| | *Helicobacter pylori* No. 5025 helical cells | — | — | — | >3.5 | — |
| | *Helicobacter pylori* No. 5049 helical cells | — | — | — | >3.5 | — |
| | *Helicobacter pylori* No. 5142 helical cells | — | — | — | >3.5 | — |
| | *Helicobacter pylori* No. 5287 helical cells | — | — | — | >3.5 | — |
| | *Helicobacter pylori* No. 5308 helical cells | — | — | — | >3.5 | — |
| | *Helicobacter pylori* No. 5314 helical cells | — | — | — | >3.5 | — |
| | *Helicobacter pylori* No. 5330 helical cells | | | | | |
| | *Bacteroides vulgatus* IFO 14291 | 0.066 | 0.066 | 0.058 | — | — |
| | *Escherichia coli* ATCC 25922 | 0.056 | 0.055 | 0.050 | — | — |
| | *Campylobacter jejuni* 80068 | 0.079 | 0.057 | 0.062 | — | — |
| | *Helicobacter felis* ATCC 49179 helical cells | 0.066 | 0.051 | 0.055 | 0.014 | 1.63 |
| | *Helicobacter hepaticus* ATCC 51448 helical cells | 0.059 | 0.049 | 0.061 | 0.016 | 0.13 |

As shown in Table 2, the monoclonal antibodies 21G2, 41A5 and 82B9 were found to show high reactivity against helical cells and coccoid cells of each of *Helicobacter pylori* strains. On the other hand, they did not react at all with *Bacteroides vulgatus, Escherichia coli, Campylobacter jejuni, Helicobacter felis* or *Helicobacter hepaticus*. On the contrary, Meridian's HpSA showed reactivity against *Helicobacter fells* and *Helicobacter hepaticus* as well.

EXAMPLE 4

[Detection of *Helicobacter pylori* in Fecal Specimens by Sandwich ELISA (1)]

Feces specimens (each 250 mg) from three persons judged as *Helicobacter pylori* positive and three persons judged as negative by the urea breath test were each suspended in 0.5 mL of 0.1% skim milk-PBS, and each suspension was tested in the same manner as in Example 2 (3). The same fecal specimens were also subjected to the test using Meridian's HpSA ELISA according to the procedure indicated, and the absorbance values at 450 nm were measured. The respective absorbance values and urea breath test results are shown in Table 3.

TABLE 3

| Combination of monoclonal antibodies | | Absorbance (urea-expired air test alone, per mil) | | | | | |
|---|---|---|---|---|---|---|---|
| Immobilized | Label | No. 1 | No. 2 | No. 3 | No. 4 | No. 5 | No. 6 |
| 21G2 | 21G2 | 0.041 | 0.043 | 0.043 | 3.3 | 2.8 | 2.1 |
| 21G2 | 41A5 | 0.092 | 0.079 | 0.075 | >3.5 | >3.5 | 2.4 |

TABLE 3-continued

| Combination of monoclonal antibodies | | Absorbance (urea-expired air test alone, per mil) | | | | | |
|---|---|---|---|---|---|---|---|
| Immobilized | Label | No. 1 | No. 2 | No. 3 | No. 4 | No. 5 | No. 6 |
| 21G2 | 82B9 | 0.071 | 0.052 | 0.067 | >3.5 | >3.5 | 3.2 |
| 41A5 | 41A5 | 0.17 | 0.17 | 0.10 | 3.3 | >3.5 | 0.84 |
| 41A5 | 21G2 | 0.077 | 0.073 | 0.080 | >3.5 | >3.5 | 1.8 |
| 41A5 | 82B9 | 0.029 | 0.053 | 0.035 | >3.5 | >3.5 | 2.2 |
| 82B9 | 82B9 | 0.12 | 0.086 | 0.071 | >3.5 | >3.5 | 2.3 |
| 82B9 | 21G2 | 0.063 | 0.082 | 0.066 | 3.3 | >3.5 | 1.1 |
| 82B9 | 41A5 | 0.079 | 0.077 | 0.064 | >3.5 | >3.5 | >3.5 |
| HpSA | | 0.077 | 0.028 | 0.025 | 1.8 | 2.5 | 1.8 |
| Urea-expired air test | | (1.0) | (0.6) | (0.9) | (17) | (26) | (17) |

The fecal specimens provided by the subjects (No. 4, 5, 6) whose urea breath test results were positive were found to show markedly higher absorbance values as compared with the negative specimens (No. 1, 2, 3).

EXAMPLE 5

[Detection of *Helicobacter pylori* in Fecal Specimens by Sandwich ELISA (2)]

(1) Monoclonal Antibody Preparation

The ascitic fluid (5 mL) recovered from a BALB/cA mouse transplanted with the hybridoma 21G2 was diluted two-fold with PBS, 10 mL of saturated ammonium sulfate was added dropwise, and the mixture was allowed to stand at 4° C. for 4 hours. The mixture was then centrifuged at 3,000 rpm for 20 minutes, the sediment was dissolved in 10 mL of PBS, and the solution was dialyzed against PBS.

(2) Preparation of Monoclonal Antibody-Immobilized Plates

The monoclonal antibody 21G2 solution prepared in (1) was immobilized on 96-well ELISA plates in the following manner. The antibody was diluted to a concentration of 5 μg/mL with PBS and the dilution was distributed in 0.2-mL portions into each well of the 96-well ELISA plates and, after overnight standing at 4° C., the plates were washed with PBS.

(3) Preparation of a Peroxidase-Labeled Monoclonal Antibody

A peroxidase-labeled monoclonal antibody was prepared using the maleimide method (Eiji Ishikawa: "Experiments in Biological Chemistry", vol. 27, Enzyme labeling techniques, p. 51, published 199 by Gakkai Shuppan Center). The monoclonal antibody (5 mg) prepared in (1) was mixed with 0.6 mg of S-acetylmercaptosuccinic anhydride (product or Aldrich) and the reaction was allowed to proceed in 0.5mL of 0.1 M phosphate buffer (pH 6.5) at 30° C. for 30 minutes. To the reaction mixture were added 20 μL of 0.1 M EDTA, 0.1 mL of 0.1 M Tris hydrochloride buffer (pH 7.0) and 0.1 mL of 1 M hydroxylamine (pH 7.0), and the mixture was allowed to stand at 30° C. for 5 minutes and then centrifuged at 10,000 rpm for 5 minutes to give a supernatant. The supernatant was subjected to ultrafiltration using Centricon 30 (product of Amicon) to thereby remove the reagents, and the solvent was replaced with 1 mL of 5 mM EDTA-0.1 M phosphate buffer (pH 6.5), whereby the thiol group-introduced monoclonal antibody.

Peroxidase (5 mg, horseradish, product of Toyobo) was mixed with 1 mg of N-succinimidyl 4-(N-maleimidomethyl)cyclohexane-1-carboxylate (product of ICN Biomedicals), and the reaction was allowed to proceed in 0.5 mL of 0.1 M phosphate buffer (pH 7.0) at 30° C. for 1 hour. The reaction mixture was centrifuged at 10,000 rpm for 5 minutes to give a supernatant. The supernatant was subjected to ultrafiltration using Centricon 30 to remove the reagents, the solvent was then replaced with 1 mL of 0.1 M phosphate buffer (pH 7.0), whereby the maleimide group-introduced peroxidase was obtained.

The above thiol group-introduced monoclonal antibody and maleimide group-introduced peroxidase were mixed together in a molar ratio of 1:5, and the reaction was allowed to proceed at room temperature for 30 minutes. The reaction mixture was applied to a gel filtration column (Sephacryl-S 300 HR column; diameter 26×length 870 mm, 0.1 M phosphate buffer (pH 6.5)) and a fraction containing the peroxidase-labeled monoclonal antibody was collected.

(4) Detection of *Helicobacter pylori* in Fecal Specimens by Sandwich ELISA

Feces specimens (each 250 mg) from ten persons judged as *Helicobacter pylori* positive and ten persons judged as negative by the urea breath test were each suspended in 0.5 mL of 0.1% skim milk-PBS, each mixture was centrifuged at 3,000 rpm for 10 minutes, and the supernatant thus obtained was used as a fecal extract. 50 μL of each fecal extract and 50 μL of the peroxidase-labeled monoclonal antibody prepared in (3) were added to each well of the above-mentioned monoclonal antibody-immobilized plate. After 1 hour of standing at 25° C., the plate was washed with 5 portions of a washing solution (0.05% Tween 20-PBS), 0.1 mL of a substrate solution (tetramethylbenzidine+hydrogen peroxide, product of BioFX) was added to each well, and the reaction was allowed to proceed at room temperature for 10 minutes. Thereafter, the enzyme reaction was terminated by adding 50 μL of 1 N sulfuric acid to each well, and the absorbance (450 nm–630 nm) was measured. The same fecal specimens were tested using HpSA and the absorbance (450 nm–630 nm) was measured. The results are shown in Table 4.

TABLE 4

| Specimen No. | Urea-expired air test Judgment[*1] (per mil) | 21G2 sandwich ELISA Judgment[*2] (Absorbance) | HpSA Judgment[*3] (Absorbance) |
|---|---|---|---|
| 1 | + (17) | + (1.89) | + (1.30) |
| 2 | + (11) | + (1.19) | + (1.57) |
| 3 | − (40) | + (1.52) | + (1.64) |
| 4 | + (40) | + (1.24) | + (2.13) |
| 5 | + (25) | + (0.46) | + (2.11) |
| 6 | + (34) | + (0.79) | + (1.37) |
| 7 | + (49) | + (1.38) | + (1.60) |
| 8 | + (50) | + (3.13) | + (2.18) |
| 9 | + (19) | + (0.36) | + (0.76) |
| 10 | + (40) | + (2.43) | + (1.97) |
| 11 | − | − (0.05) | − (0.01) |
| 12 | − | − (0.02) | − (<0.01) |
| 13 | − | − (0.04) | − (<0.01) |
| 14 | − | − (0.09) | − (0.01) |
| 15 | − | − (0.02) | − (<0.01) |
| 16 | − | − (0.03) | + (0.27) |
| 17 | − | − (0.02) | − (<0.01) |
| 18 | − | − (0.04) | − (0.01) |
| 19 | − | − (0.05) | + (0.23) |
| 20 | − | − (0.01) | − (0.02) |

[*1]: + Positive (>5 per mil), − Negative
[*2]: + Positive (>0.1), − Negative
[*3]: + Positive (>0.1), − Negative As shown in Table 4, the sandwich ELISA using the monoclonal antibody 21G2 singly showed high reactivity with the fecal specimens from persons infected with *Helicobacter pylori* in precise agree-ent with the judgment results of the urea breath test. On the other hand, HpSA gave disagreements (false positives) with two specimens (specimen Nos. 16 and 19).

EXAMPLE 6

[Detection of *Helicobacter pylori* in Fecal Specimens by Immunochromatography]

(1) Preparation of Antibody-Immobilizing Supports

For preparing antibody-immobilizing supports with the anti-*Helicobacter pylori* monoclonal antibody and anti-rabbit IgG antibody immobilized thereon in series, a nitrocellulose sheet (product of Whatman) was cut to 5 mm×20 mm, and a solution of the monoclonal antibody 21G2 was applied to each piece at a site 10 mm from the bottom, and a solution of goat anti-rabbit IgG polyclonal antibody (product of Cappel) at a site 15 mm from the bottom, using Biojet Q 3000 (product of Biodot). After 2 hours of drying at room temperature, each sheet was blocked by 10 minutes of immersion in 1% skim milk (product of Difco)–0.1% Tween 20-PBS, followed by thorough drying.

(2) Preparation of a Colored Latex Particle-Labeled Product a. Red Latex Particle-Labeled Anti-*Helicobacter pylori* Antibody PBS (1.2 mL) was added to 300 μL of a red latex particle dispersion (PL-Latex, 10%, 450 nm, product of Polymer Laboratories), and the mixture was centrifuged at 13,000 rpm for 5 minutes. To the sediment was added 1 mL of a solution of the monoclonal antibody 21G2 (5 mg/mL) and, after thorough mixing, the reaction was allowed to proceed at room temperature for 1 hour. For removing the unreacted portion of the monoclonal antibody, centrifugation was carried out at 13,000 rpm for 5 minutes, the sediment was suspended in 1.5 mL of PBS, and the suspension was again centrifuged. Blocking was effected by adding 1 mL of 1% skim milk and allowing the reaction to proceed at room temperature for 1 hour. Thereafter, centrifugation was carried out ae 13,000 rpm for 5 minutes, and the sediment was suspended in 1.5 mL of PBS containing 1% skim milk-0.01% sodium azide.

b. Blue Latex Particle-Labeled Rabbit IgG

Blue latex particle-labeled rabbit IgG was prepared using a blue latex particle dispersion (PL-Latex, 10%, 450 nm, product of Polymer Laboratories) and rabbit IgG (0.5 mg/mL, product of Cappel) and following the same procedure as mentioned above.

c. Colored Latex Particle-Labeled Product

Equal amounts of the above two kinds of colored latex particle-labeled antibody were mixed up, and 5 mm×5 mm pieces of Bemliese (registered trademark) nonwoven fabric (product of Asahi Kasei Co.) were impregnated with 10 μl of the mixture and then air-dried.

(3) Preparation of Immunochromatographic Test Pieces

The colored latex particle-labeled product was overlaid on the antibody-immobilizing support to a site of 2.5 mm from the bottom. Further, a carrier (3 MM Chr, product of Whatman) for immersing in the test solution was further overlaid on the colored latex-labeled product to a site of 2.5 mm from the bottom. A water-absorbing carrier (3 MM Chr, product of Whatman) was overlaid on the antibody-immobilizing support to a site of 2 mm from the top and, finally, all the members were fixed by covering with a transparent adhesive tape, to give an immunochromatographic test piece.

(4) Detection of *Helicobacter pylori* in Fecal Specimens

Tests were carried out using feces from the six persons (3 positive and 3 negative) described in Example 4. A 0.1-g portion of each fecal specimen was taken and suspended in 1 ml of 0.1% BSA-0.05% Tween 20-PBS. Impurities were removed by 1 minute of centrifugation at 3,000 rpm, and 50 μL of the supernatant was dropped onto the immunochromatographic test piece prepared in (3) at a site on the carrier for immersing in the test solution. Ten minutes later, judgment was made as to whether a red line had appeared at the site of immobilization of the anti-*Helicobacter pylori* monoclonal antibody. As a result, such red line could not be observed for each of the negative specimens while a red line could be confirmed for all the positive specimens. With all specimens, a blue line was confirmed. The test was thus successful.

EXAMPLE 7

[Detection of *Helicobacter pylori* in Fecal Specimens by the Latex Agglutination Method]

(1) Preparation of a Latex Particle-Labeled Anti-*Helicobacter pylori* Antibody

PBS (0.4 mL) was added to 0.1 mL of a white latex particle dispersion (PL-Latex, 10%, 440 nm, product of Polymer Laboratories), and the mixture was centrifuged at 13,000 rpm for 5 minutes. To the sediment were added 0.5 mL of PBS and 0.5 mL of a solution of the monoclonal antibody 21G2 (1 mg/mL) and, after thorough mixing, the reaction was allowed to proceed overnight at room temperature. For removing the unreacted portion of the monoclonal antibody, centrifugation was carried out at 13,000 rpm for 10 minutes, the sediment was suspended in 1 mL of PBS, and the suspension was again centrifuged. Blocking was effected by adding 1 mL of 1% skim milk and allowing the reaction to proceed at room temperature for 1 hour. Thereafter, centrifugation was carried out at 13,000 rpm for 5 minutes, and the sediment was suspended in 1 mL of PBS containing 1% skim milk-0.01% sodium azide.

(2) Detection of *Helicobacter pylori* in Fecal Specimens

Tests were carried out using feces from the six subjects (3 positive and 3 negative) described in Example 4. A 0.1-g portion of each fecal specimen was taken and suspended in 1 mL of PBS containing 0.1% BSA-0.05% Tween 2.0. Impurities were removed by 1 minute of centrifugation at 3,000 rpm, and the supernatant was obtained. A 50-μL portion of this supernatant of fecal suspension and 50 μuL of the latex particle-labeled anti-*Helicobacter pylori* antibody prepared in (1) were dropped onto a latex agglutination board and mixed up using a slide rotor (product of Eiken Chemical). Five minutes later, judgment was made as to the occurrence or nonoccurrence of agglutination by visual observation. As a result, no agglutination was observed with any of the negative specimens, while agglutination was confirmed with all the positive specimens.

EXAMPLE 8

[Molecular Weight Determination of the Antigen in Feces by Gel Filtration]

Twenty grams of feces specimens provided by *Helicobacter pylori*-positive persons (No. 4 and No. 5 in Table 3) were suspended in 100 mL of ice-cooled PBS. Centrifugation was carried out at 10,000×g for 10 minutes, the sediment was discarded, and centrifugation was again carried out at 90,000×g for 30 minutes to give a supernatant. A 1.5-mL portion of this supernatant was applied to a gel filtration column packed with Sephacryl-S300HR (product of Pharmacia) (1.5×140 cm, 0.1 M phosphate buffer, pH 6.5) and 1.5-mL fractions were collected. The molecular weight markers used were thyroglobulin, ferritin, catalase, bovine serum albumin and cytochrome c. Each fraction was tested for antigen detection by the sandwich ELISA mentioned in Example 2 (3) (monoclonal antibody 41A5-immobilized plate, biotin-labeled monoclonal antibody 8239, ard monoclonal antibody 21G2-immobilized plate and biotin-labeled monoclonal antibody 41A5). As a result, *Helicobacter pylori*-specific antigen in feces was found to have a molecular weight of 270 kDa.

EXAMPLE 9

[Antigen Identification]

(1) Antigen Purification

A column (10 mL) was prepared by immobilizing the monoclonal antibody 82B9 on CNBr-activated Sepharose 4B (product of Amersham Pharmacia Biotech) according to the method described in Amersham Pharmacia Biotech's Affinity Chromatography Handbook. *Helicobacter pylori* (ATCC 43504) cells were disrupted by sonication and subjected to ultracentrifugation, and 5 mL of the supernatant obtained (protein concentration 4 mg/mL) was applied to the above column. After 2 hours of standing at room temperature, the column was washed with 120 mL of PBS (flow rate about 2 mL/minute) and eluted with 130 mL of 0.2 M glycine HCl buffer (pH 3.0). The washings and eluate were respectively collected as 10-mL fractions and each fraction was measured for absorbance (280 nm) and antigenicity. The antigenicity determination was carried out by the sandwich ELISA (immobilized 21G2, and 82B9 as label) described in Example 2. As shown in FIG. 1, the antigenicity was confirmed in eluate fractions (fractions Nos. 14 to 17) alone.

(2) Purity and Molecular Weight of a Purified Antigen

An eluate fraction (No. 14; 50 μL) was admixed with an equal amount of a sample buffer (2% SDS-5% mercaptoethanol), and the mixture was boiled at 100° C. for 5 minutes. A 20-μL portion of this solution was subjected to SDS-polyacrylamide gel electrophoresis (4–20% acrylamide gel). The molecular weight markers used were phosphorylase b, bovine serum albumin, egg white albumin, carbonate dehydratase, soybean trypsin inhibitor and α-iactoalbumin. After electrophoresis, the gel was stained watt Silver-Stain KANTO III (product of Kanto Chemical). As a result, the purified antigen gave a single bard and its molecular weight was 59 kDa. Further, 1 mL of the eluate fraction (No. 14) was subjected to gel filtration on Sephacryl-S300HR in the same manner as described in Example 6. The fraction obtained was tested for antigenicity by sandwich ELISA and, as a result, this purified antigen was found to have a molecular weight of 270 kDa and to be the same one as the antigen in feces.

(3) Amino-Terminal Amino Acid Sequence Determination of the Purified Antigen

Using 300 μL of the eluate fraction (No. 14), the amino-terminal amino acid sequence of the purified antigen was determined using the HP G1005A Protein Sequencing System (product of Hewlett-Packard). The sequence of the eight residues from the amino terminus was found to be Met-Val-Asn-Lys-Asp-Val-Lys-Gln. This sequence is in complete agreement with the amino-terminal sequence of Helicobacter pylori catalase (J. Bacteriol. (1996), 178, 6060–6967).

(4) Catalase Activity and Ultraviolet-Visible Absorption Spectrum Measurements of the Purified Antigen Since the amino-terminal amino acid sequence of the purified antigen was in agreement with that of catalase, each fraction was assayed for catalase activity. The reaction solution used was 11 mM hydrogen peroxide-containing PBS. Each fraction was diluted 100-fold with PBS, and the reaction was started by adding 50 μL of the dilution to 2 mL of the reaction solution. The reaction was carried out at room temperature. Absorbance measurements were carried out at 240 nm at timed intervals, and the decrements in absorbance per minute were determined. 235 was used as the blank. As a result, catalase activity was detected in the antigen fractions, as shown in FIG. 1.

For identifying he hem contained in the catalase, the ultraviolet visible absorption spectrum of the eluate fraction No. 14 was measured. As a result, absorption maxima were observed at 407 and 277 nm. These values were very similar to the literature values for Helicobacter pylori catalase (405 and 280 nm, J. Gen. Microbiol. (1991), 137, 57–61).

(5) Storage Stability of the Purified Antigen

The eluate fraction (No. 14) was diluted to 1.4 μL/mL with 0.1% BSA-containing PBS, and the solution was stored at 25° C. for 1 week. After storage, the purified antigen was assayed for antigenicity by the sandwich ELISA described in Example 5 and for catalase activity by the method described above in (4). When compared with the purified antigen frozen stored at −80° C., there was little change in antigenicity after storage at 25° C. However, the catalase activity showed a marked decrease and the residual activity was not more than 5%.

EXAMPLE 10

[Reactivity of the Anti-Helicobacter pylori Monoclonal Antibodies with the Subunit of the Antigen in Feces]

For estimating the reactivity of the anti-Helicobacter pylori monoclonal antibodies with the subunit of the antigen in feces, 50 μL of the fecal suspension supernatant from each of the Helicobacter pylori-positive subjects described in Example 8 was subjected to SDS-polyacrylamide gel electrophoresis as described in Example 9 (2). As a control, 50 μL of the purified antigen of Example 9 (eluate fraction No. 14) was also electrophoresed in the same manner. After electrophoresis, proteins were transferred to a nitrocellulose membrane by the western blotting technique. The nitrocellulose membrane was immersed in 1% skin milk for 1 hour for blocking, and then reacted with the monoclonal antibody 21G2 or 82B9 for 1 hour. The nitrocellulose membrane was washed with five portions of 0.05% Tween 20-PBS, and then reacted with the peroxidase-labeled anti-mouse IgG antibody. The nitrocellulose membrane was washed with five portions of 0.05% Tween 20-PBS and, after addition of a substrate solution (peroxide+3,3'-diaminobenzidine) incubated for 10 minutes. Either of the lanes resulting from migration of the fecal antigen and purified antigen did not show any antigenicity-due color development with any monoclonal antibody. For ascertaining the cause of failure in detecting the antigenicity of the subunit molecule, whether a treatment for dissociation into subunits causes changes in antigenicity or not was examined by the dot blotting technique. Thus, 5-μL portions of the specimens before and after dissociation treatment with 1% SDS were dropped onto a nitrocellulose membrane. After air drying, the proteins adsorbed on the nitrocellulose membrane were assayed for antigenicity by the same method as mentioned above. As a result, it was found that both the fecal antigen and purified antigen show marked decreased in antigenicity after dissociation treatment with 1% SDS. It is therefore suggested that the monoclonal antibodies of the present invention do not recognize the subunit of catalase, namely the epitope of the primary structure, but recognize a more native, higher structure as the epitope.

EXAMPLE 11

[Purification of the Antigen in Feces]

(1) Molecular Weight of the Antigen in Feces

Feces (165 g) provided by a positive subject with the highest Helicobacter pylori antigen level in feces (Specimen No. 8 in Table 4) were suspended in PBS (4 times the weight of feces), and the suspension was centrifuged (7,000 rpm, 30 minutes) to give a supernatant, which was further ultracentrifuged (30,000 rpm, 30 minutes) to give a supernatant. Ammonium sulfate (165 g) was added to 680 mL of the supernatant to attain 40% saturation, the mixture was stirred, and the resulting precipitate was removed by centrifugation (7,000 rpm, 30 minutes). To 750 mL of the supernatant was added ammonium sulfate (214 g) to attain 80% saturation, the mixture was stirred, and the resulting precipitate was recovered by centrifugation (7,000 rpm, 30 minutes). The precipitate was suspended in PBS and dialyzed against 10 L of distilled water. A 2-mL portion of the dialyzate (82 mL) was subjected to gel filtration on a Sephacryl-S300HR column in the same manner as in Example 6. The fractions obtained were examined for antigenicity by sandwich ELISA in the same manner as in Example 5. The molecular weight of the fecal antigen was found to be 270 kDa, thus identical to the molecular weight of the fecal antigen of the two positive persons described in Example 8 and of the purified antigen described in Example 9.

(2) Purification of the Antigen in Feces

A 40-mL portion of the dialyzate described in (1) was diluted to 100 mL with 10 mM phosphate buffer (pH 7.0), and the dilution was applied to a column (1×2.5 cm) packed with a cation exchange resin, CM-Sephadex C-50 (product of Amersham Pharmacia Biotech), and equilibrated with the same buffer. After washing with 10 mL of the same buffer, elution was carried out with 10 mL of PBS. The effluent, washing and eluate fractions were each 320-fold diluted with PBS containing 0.1% skim milk and then assayed for antigenicity by the sandwich ELISA described in Example 5. Antigenicity was found in the eluate fraction.

Figure 2:
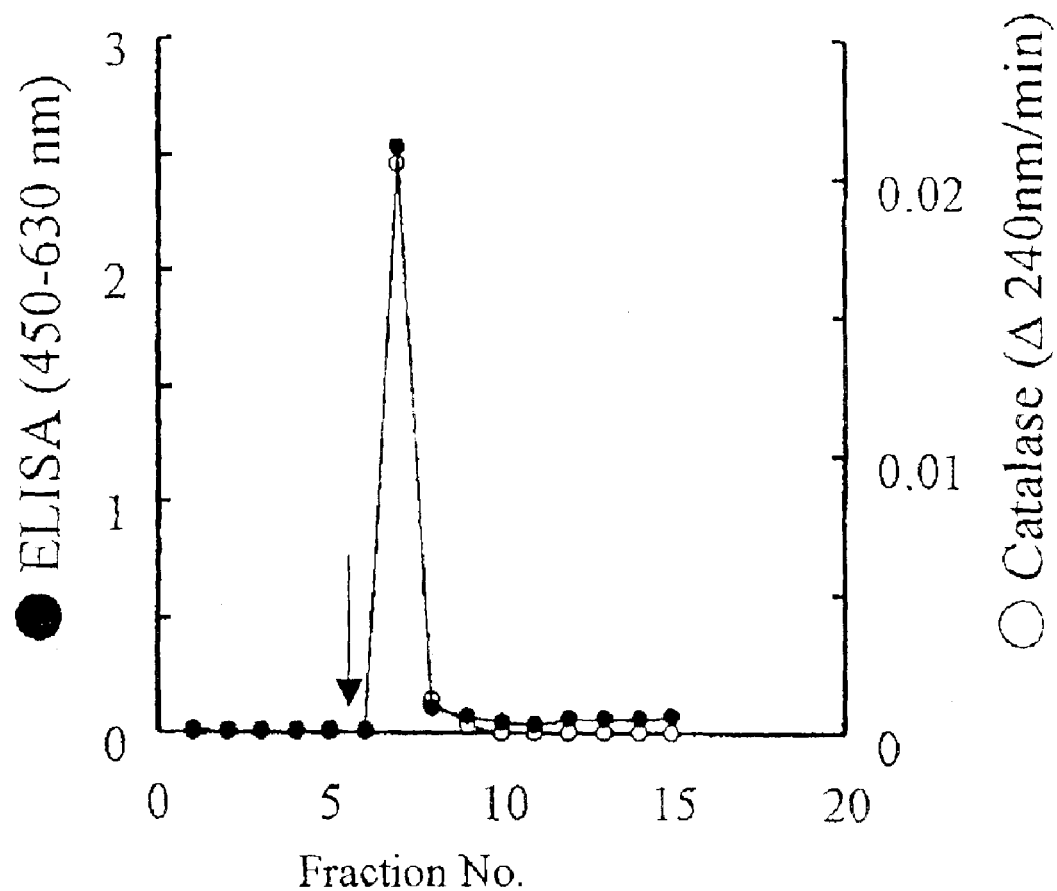
FIG. 2 illustrates the elution pattern in affinity chromatography as observed in Example 11.

A column (2×3 cm) was prepared by immobilizing the monoclonal antibody 21G2 on CNBr-activated Sepharose 43 (product of Amersham Pharmacia Biotech) according to the method described in Amersham Pharmacia Biotech's Affinity Chromatography Handbook. A 6-mL portion or the above eluate fraction was applied to the monoclonal antibody-immobilized column. After 2 hours of standing at room temperature, the column was washed with 50 mL of PBS and then eluted with 0.2 M glycine HCl buffer (pH 3.0), and 10 mL fractions were collected. Each fraction was 10-fold diluted with PBS containing 0.1% skim milk, and the dilution was assayed for antigenicity by the sandwich ELISA described in Example 5. Catalase activity was assayed by the method described in Example 9. As a result, as shown in FIG. 2, antigenicity was observed in eluate fractions (fractions Nos. 7 and 8) collected immediately after the start of elution indicated by an arrow. Catalase activity was found in agreement with the antigenicity. In view of the foregoing, this fecal sample was found to contain a native antigen having four subunits and having catalase activity.

INDUSTRIAL APPLICABILITY

The invention, which has the constitution mentioned above, can provide monoclonal antibodies capable of recognizing the epitope occurring specifically in *Helicobacter pylori* catalase. Further, by using the monoclonal antibodies of the invention, it is possible to very specifically recognize *Helicobacter pylori*. Hybridoma lines producing monoclonal antibodies recognizing *Helicobacter pylori* catalase have successfully been established, so that the same monoclonal antibodies can be produced semi-permanently. The diagnosis kit in which the monoclonal antibody of the invention is used can use digestive tract excreta as specimens and can detect *Helicobacter pylori* infection in a simple and efficient manner without causing pain on subjects. Even when only one monoclonal antibody species is used, the diagnosis kit of the invention shows very good precision, shows no difference among lots, is stable and can detect *Helicobacter pylori* infection always specifically and with great accuracy.

What is claimed is:

1. A test method for detecting a native *Helicobacter pylori* catalase in feces which comprises:

(a) contacting a fecal specimen from a patient suspected of *Helicobacter pylori* infection with at least one monoclonal antibody against the native *Helicobacter pylori* catalase to form a complex of the antibody and the antigen; and (b) detecting said antibody-antigen complex, thereby determining the presence of native *Helicobacter pylori* catalase in said fecal specimen.

2. The test method according to claim 1, wherein the at least one monoclonal antibody is produced by at least one hybridoma selected from the group consisting of hybridoma 21G2 (Deposit No. FERM BP-7336), 41A5 (Deposit No. FERM BP-7337), and 82B9 (Deposit No. FERM BP-7338).

3. The test method according to claim 1 or 2, wherein said test method comprises an ELISA technique.

4. The test method according to claim 1 or 2, wherein said test method comprises an immunochromatography technique.

5. A diagnosis kit for detecting a native *Helicobacter pylori* catalase in a specimen, which comprises at least one monoclonal antibody produced by at least one hybridoma selected from the group consisting of hybridoma 21G2 (Deposit No. FERM BP-7336), 41A5 (Deposit No. FERM BP-7337), and 82B9 (Deposit No. FERM BP-7338).

6. The diagnosis kit according to claim 5, which further comprises a means for carrying out an ELISA technique.

7. The diagnosis kit according to claim 5, which further comprises a means for carrying out an immunochromatography technique.

8. A hybridoma which is 21G2 (Deposit No. FERM BP-7336), 41A5 (Deposit No. FERM BP-7337), or 82B9 (Deposit No. FERM BP-7338).

9. A monoclonal antibody which is produced by the hybridoma according to claim 8.

* * * * *